United States Patent [19]

Schoolman et al.

[11] Patent Number: 5,127,411

[45] Date of Patent: Jul. 7, 1992

[54] ORAL APPLIANCE FOR REMOVING AEROSOLS PRODUCED DURING DENTISTRY

[76] Inventors: Arnold Schoolman, 1000 E. 50th, Ste. 310, Kansas City, Mo. 64110; Ron Geistfeld, 740 River Dr., #21D, St. Paul, Minn. 55116

[21] Appl. No.: 725,197

[22] Filed: Jul. 1, 1991

Related U.S. Application Data

[63] Continuation-in-part of Ser. No. 552,150, Jul. 12, 1990, Pat. No. 5,052,411, and a continuation-in-part of Ser. No. 256,629, Oct. 12, 1988.

[51] Int. Cl.$^5$ .............................. A61B 19/00
[52] U.S. Cl. ...................... 128/863; 433/91; 128/917
[58] Field of Search ............ 433/91, 92, 93, 94, 433/95; 128/863, 910, 205.27, 205.28, 205.29, 206.22, 917

[56] References Cited

U.S. PATENT DOCUMENTS

| | | | |
|---|---|---|---|
| 3,027,643 | 4/1962 | Cohen | 433/93 |
| 3,537,447 | 11/1970 | Gauthier | 128/847 |
| 3,625,207 | 12/1971 | Agnew | 128/863 X |
| 3,763,857 | 4/1972 | Schrading | 128/853 |
| 3,768,477 | 10/1973 | Anders et al. | 433/91 |
| 3,881,477 | 5/1975 | Von Otto | 128/847 |
| 4,053,984 | 10/1977 | Moss | 433/93 |
| 4,055,173 | 10/1977 | Knob | 128/847 |
| 4,082,092 | 4/1978 | Foster | 128/847 |
| 4,140,105 | 2/1979 | DuBois | 128/847 |
| 4,223,669 | 9/1980 | Morledge | 128/847 |
| 4,240,789 | 12/1980 | Rosenthaler | 433/93 X |
| 4,250,882 | 2/1981 | Adair | 604/355 |
| 4,252,054 | 2/1981 | Bakels | 433/92 |
| 4,446,861 | 5/1984 | Tada | 128/863 |
| 4,650,171 | 3/1987 | Howorth | 5/600 |
| 4,770,169 | 9/1988 | Schmoegner et al. | 128/910 X |
| 4,895,172 | 1/1990 | Lindkuist | 128/863 |

FOREIGN PATENT DOCUMENTS

| | | | |
|---|---|---|---|
| 524888 | 4/1955 | Italy | 433/93 |
| 204376 | 8/1939 | Switzerland | 433/91 |
| 207668 | 11/1939 | Switzerland | 433/91 |

*Primary Examiner*—Robert A. Hafer
*Assistant Examiner*—Kevin G. Rooney
*Attorney, Agent, or Firm*—Litman, McMahon & Brown

[57] ABSTRACT

An apparatus to aid in isolating a medical practitioner from infectious materials found in a patient. The apparatus includes a collector for providing a vacuum barrier around the mouth of a patient to trap aerosols and the like emanating from the patient during a dental procedure. The collector is flow connected to a vacuum source for drawing a vacuum, and gases drawn in by the source are passed through a filter. The collector is ring-shaped to surround the mouth and to allow the practitioner to see into the site of the procedure and is disposable after each operation.

23 Claims, 2 Drawing Sheets

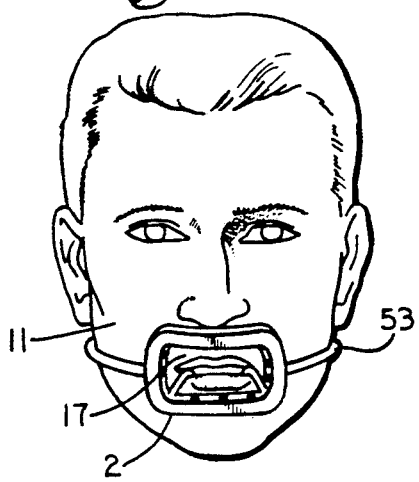
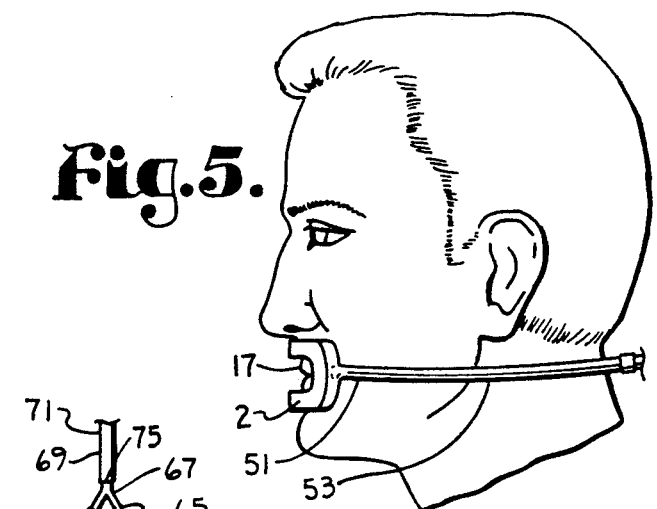
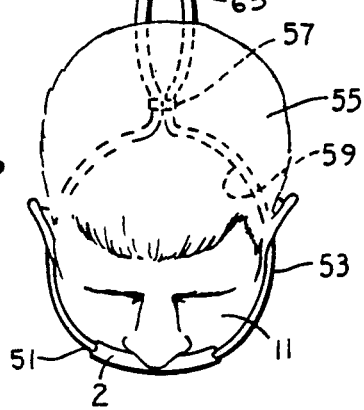
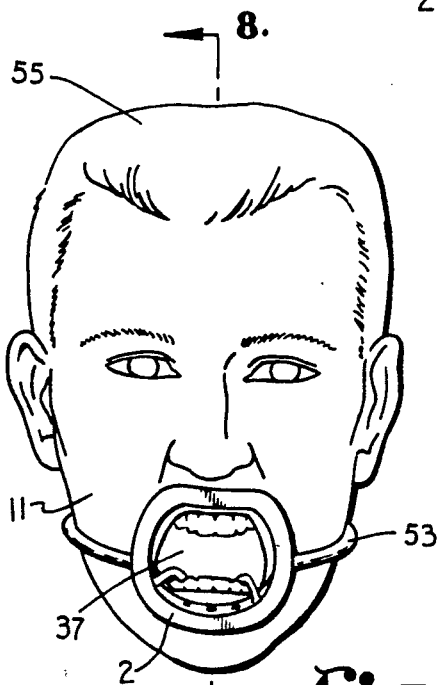
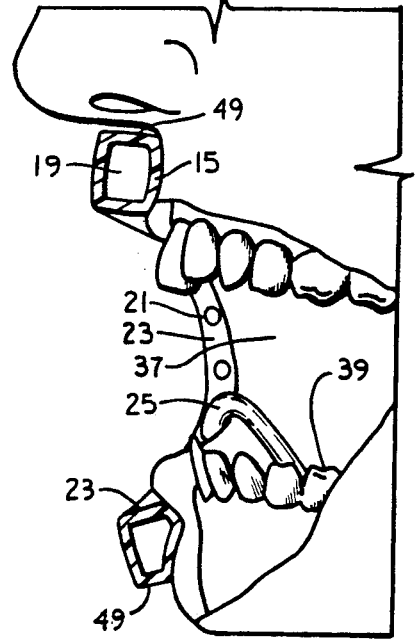

ORAL APPLIANCE FOR REMOVING AEROSOLS PRODUCED DURING DENTISTRY

CROSS-REFERENCE TO RELATED APPLICATIONS

The present application is a continuation-in-part of U.S. application Ser. No. 07/552,150, filed on Jul. 12, 1990, entitled Vacuum Barrier Attachment for Medical Equipment, now patent No. 5,052,411 and application Ser. No. 07/256,629 filed on Oct. 12, 1988, entitled Vacuum Strip Apparatus for Surgery.

BACKGROUND OF THE INVENTION

The present invention relates to Ventilating systems for protecting dental practitioners from contaminants, including harmful aerosols, blood and other substances created during dental procedures and the like emanated by patients and, in particular, an apparatus for producing a vacuum barrier to protect dental practitioners from air borne contaminants released during dental procedures.

The medical and dental communities have long recognized the need to shield practitioners from harmful substances, such as: noxious gases, infected body fluids, tissue debris and bone chips that are produced in medical and dental procedures. Many previous systems have been designed to draw a vacuum in order to remove harmful substances emanating from a patient (for example, U.S. Pat. No. 3,537,447 of Gauthier). Although the prior art systems provide dental practitioners with some protection, the recent Acquired Immune Deficiency Syndrome (AIDS) epidemic has produced the need for providing greater protection for health care workers. The present technology is inadequate for this purpose.

In particular, dental procedures such as drilling, cutting with a reciprocating saw or the like which are common procedures for dentists and oral surgeons produce an aerosol of human tissue that becomes suspended in the air around the site of the operation and which may contain AIDS virus, if the patient is infected. Such aerosols often include powdered bone or blood, both of which carry the AIDS producing virus, if the patient is infected. Such aerosols can come into contact with mucus membranes of personnel in the operating field and may infect such personnel with the AIDS producing virus or other infectious diseases.

At the time of filing of the present application, it is estimated that AIDS has already claimed over 100,000 lives in the United States and an estimated 1.5 million Americans have become infected with the human immunodeficiency virus (HIV). The virus which is transmitted through body fluids has been isolated in blood, semen, saliva, tears, urine, cerebrospinal fluid, cervical secretions, breast milk, bone and other tissues. There are reported cases of HIV infections acquired by health care workers through direct percutaneous exposure to HIV infected body fluids or particles.

To shield health care workers from the AIDS virus, special precautions in the use of surgical and dental equipment should be taken. As was noted above, use of dental equipment often results in the release of AIDS or otherwise infected material from a patient into aerosols in the surrounding air.

This is especially true with the use of medical drills, routers and saws, which produce in the surrounding area a fine aerosol of fluids, tissue and bone chips, or may even cause a stream of blood to spurt into the air. Aerosolization of the AIDS virus may occur during the use of surgical power instruments. Such airborne viruses float around the operating room and may encounter and invade a dental practitioner in the room.

In light of the deadliness of the AIDS virus and the need to remove virtually all of the virus-carrying aerosol produced in a dental procedure, present systems are inadequate. Conventional barriers, whether physical or vacuum-producing, that are situated away from the operating site, either limit visibility and/or mobility or expose the operator to the possibly infected aerosol. When using surgical and dental equipment, a dental practitioner must often work between the vacuum source or physical barrier and the mouth of the patient, thus exposing the practitioner to infection. The barrier may also restrict the practitioner's view or movement of the tool.

Point of operation protection is needed without significant loss of mobility and/or visibility. Vacuum barriers placed directly into the patient's mouth are not well suited for drawing in airborne contaminants, and may impair access to the operating site for some dental procedures. Vacuum barriers positioned on the instrument itself typically limit the area of protection however, a vacuum barrier placed near the point of operation without unduly restricting mobility and/or visibility is possible.

SUMMARY OF THE INVENTION

The present invention provides a ventilation apparatus which is adapted to more efficiently and effectively remove contaminants emitted from the mouth of a dental patient undergoing a dental treatment, including oral surgery. The apparatus includes an annular collector designed to sealably fit around the mouth of the patient on the skin of the patient surrounding the mouth and which creates a vacuum barrier to draw contaminants away from the dental practitioner. The dental practitioner is allowed full freedom of movement relative to the performance of dental procedures, as the collector is mounted on the patient in such a manner that the dental practitioner does not have to work under or around a prepositioned shield. Also, visibility of the operating site is maintained by constructing the collector as a ring-shaped tubular member surrounding the mouth, thereby providing visibility and access to the operating site.

The collector is constructed such that debris and aerosols passing into the air from the operating site are drawn by suction into the apparatus and away from the practitioner. The suction produced by the apparatus draws aerosols and fluids through at least one aperture in the collector and into the internal channel of the collector and away from the dental practitioner's face and body, thereby creating a "vacuum barrier" with respect to aerosols escaping from the site of the dental procedure that otherwise would be allowed to reach the practitioner.

Preferably, the interior wall of the collector has a plurality of spaced apertures therealong suited to collect both aerosols in the air and saliva or other liquids seeping from the patient's mouth. A pair of tubes are also connected to the vacuum source through the collector and positioned to extend into the lower par of the mouth of the patient to collect saliva and other liquids.

The specific design of the apparatus, including the size and shape of the aerosol collector and method of its attachment, are somewhat dependent upon the size and physical characteristics of the patient, as well as the requirements of the specific dental procedure for which the ventilating apparatus is to be used. Although specific designs will vary, each apparatus has an aerosol collector with at least one suction aperture directed to produce a suction between the operating site and the dental practitioner when in use and in flow communication with a suction hose and a vacuum source.

The suction hose includes segmented flexible tubing connecting the annular collector with the vacuum source such that during operation of the apparatus, the vacuum source operably draws solid, liquid and gaseous materials through the suction aperture of the collector while the collector is in a surrounding relationship to the site of the dental procedure. Contaminants drawn in through the suction aperture can then be removed by a filter system incorporated in the suction hose. The filter is removably connected to other components of the suction hose. A dental practitioner may remove the filter and mail it to a laboratory for pathological analysis after use. Such an analysis can be anonymous in order to determine the incidence of a particular disease in the population as a whole or specific with the patient receiving the results.

The vacuum source or pump which generates the negative pressure for drawing contaminants into the suction aperture of the apparatus may be of the type commonly available as commercial or household vacuum cleaner designed for removing solids and liquids from the environment. The vacuum source should include a reservoir for collecting fluids drawn through the apparatus. A solution of sodium hypochlorite, such as sold under the trademark "Clorox," is preferably added to the reservoir so as to further ensure that the gases exiting the system and the fluids collected in the reservoir of the vacuum source are disinfected. The apparatus is removably attached to the patient, and except for the vacuum source, such as a pump, is readily disposable by incinerator or the like in such a manner as to destroy any contamination therein.

OBJECTS AND ADVANTAGES OF THE INVENTION

The principal objects of the present invention are: to provide a ventilating device for use in shielding an operator of dental equipment or related tools from harmful substances produced during the use of the equipment; to provide such a device which will maintain adequate visibility and mobility for the operation of dental equipment or related tools, while increasing protection; to provide such a device which can be maintained in an operative position between the patient and normally all of the dental practitioner without overly interfering with the movement of the dental practitioner in operating dental equipment or related tools; to provide such a device which offers a vacuum barrier that positively and effectively draws air away from a dental or surgical site so as to protect the dental practitioner from aerosols and other emissions from the site; to provide such a device which can be adapted for use with different sizes and physical conditions of patients; to provide such a device which can be adapted for use with different dental procedures to provide such a device which may include a small, removable filter which may be sent through the mail to a laboratory for pathogenic analysis; and to provide such a device which is relatively inexpensive to manufacture, easy to set up and use, and particularly well adapted for the intended usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 4 is a front elevational view of the collector of the apparatus operably positioned about the patient's closed mouth.

FIG. 5 is a side elevational view of the collector of the apparatus operably positioned about the patient's mouth.

FIG. 6 is a top plan view of the collector portion of the apparatus and illustrates in phantom lines the routing of conduits connected to the collector about the perimeter of the patient's head.

FIG. 7 is an enlarged front elevational view of the collector portion of the apparatus and illustrates the resilience thereof with the patient's mouth open.

FIG. 8 is an enlarged cross-sectional view of the collector, taken along line 8—8 of FIG. 7, and illustrates details of the collector portion of the apparatus with the patient's mouth in an open position and partly broken away to show details thereof.

DETAILED DESCRIPTION OF THE INVENTION

Figure 1:
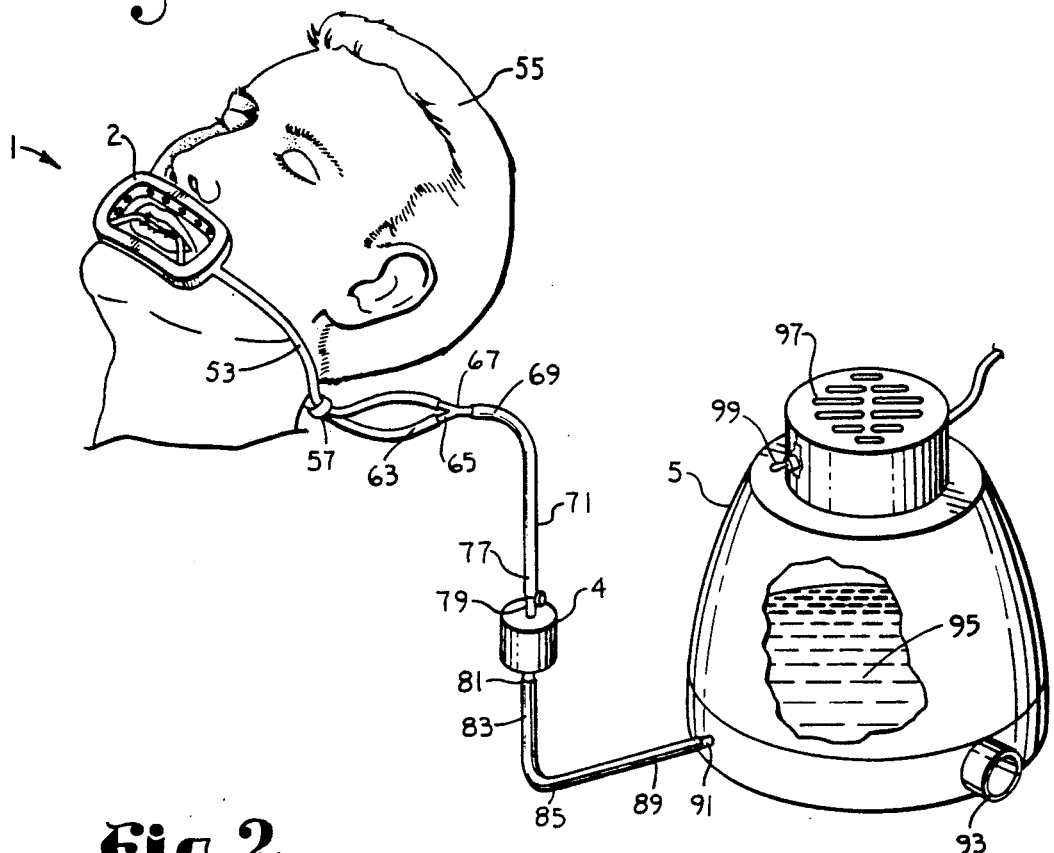
FIG. 1 is a perspective view of an apparatus for creating a vacuum barrier during dentistry which embodies the present invention secured to and positioned about the mouth of a dental patient.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in detail, the reference numeral 1 generally designates an appliance or device for producing a vacuum barrier during dentistry according to the present invention. The apparatus 1 includes a suction producing member that in the present embodiment is illustrated as an annular dental collector 2, conduit means that in the present embodiment is illustrated as a branched and segmented hose 3 incorporating filter means 4, and suction pump means such as vacuum pump 5. The reference numeral 7 generally designates a dental patient. Various gases, aerosols and fluids emanating from the patient 7 having potentially hazardous contaminants therein are drawn into the collector 2. The contaminants may be aerosolized debris formed during a dental procedure, and may include pathogenic bacteria, viruses, or other hazardous material or the like. It is also foreseen that the contaminants may be in the form of a liquid due to bleeding, salivation, irrigation by the dentist or the like. It is also foreseen that the contaminants may be in the form of gases used to anesthetize the patient 7.

FIG. 1 illustrates the annular collector 2 operably mounted on a dental patient's face 11. The collector 2 is in the form of a hollow or tubular member of endless configuration defining and surrounding an access passageway or opening 13. An engagement surface 15 of the collector 2 is sealably mounted on the patient's face 11, with the central access opening 13 of the collector 2 located above and generally surrounding a perioral area 17 of the face 11, which constitutes or includes the primary dental or surgical field to be isolated by the apparatus 1.

Figure 2:
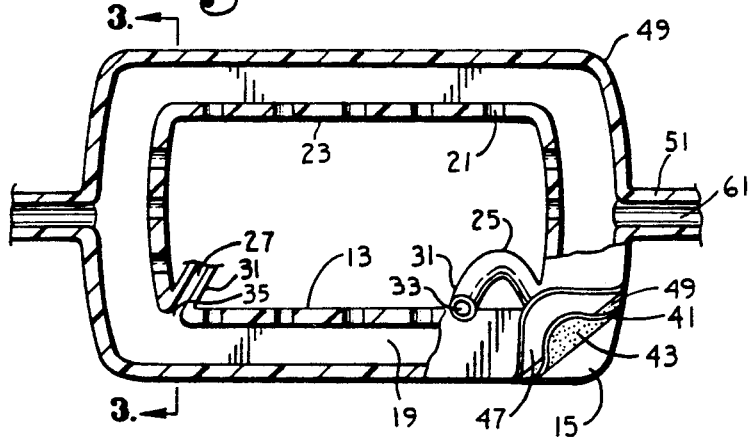
FIG. 2 is an enlarged fragmentary rear elevational view of a collector of the apparatus with a side wall broken away to illustrate air flow passages.
Figure 3:
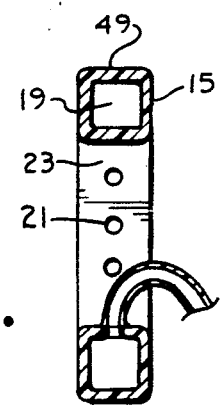
FIG. 3 is an enlarged cross-sectional view of the collector, taken along line 3—3 of FIG. 2, and showing a cross-section of an auxiliary tube communicating with the air flow passages of the collector.

The collector 2 has an internal chamber or channel 19 communicating with the surrounding environment through a plurality of generally equally sized ports or apertures 21 positioned at spaced locations along the inwardly facing surface 23 which defines and circumscribes the access opening 13. As is illustrated by FIGS. 2 and 8, the collector 2 includes two flexible and resilient auxiliary tubes 25 each having a central lumen or bore 27, a first end 29, and a second end 31. The bore first end 29 has a distal opening 33 and the second end 31 has an opening 35 therein. The opening 33 of the first end 29 of each auxiliary tube 25 is operably positioned for drawing fluids from the mouth 37 of the patient 7. The second end 31 of the auxiliary tube 25 is connected to the inwardly facing surface 23 of the collector 2 and is operably flow connected to internal channel 19 therein.

The collector 2 is preferably formed of polysilicone, but may be formed of any other medically acceptable pliable, moisture resistant and substantially fluid impervious material having sufficient resilience and flexibility to move or flex with and conform to the varying contours of the face 11 of the patient 7 to which it is applied, especially as the mouth 37 of the patient 7 is opened and closed.

While the accompanying drawings illustrate the collector 2 as it would appear having two auxiliary tubes 25 positioned such that they project into the mouth 37, extending generally into a submandibular space 39, it is foreseen that the collector 2 could be manufactured without the auxiliary tubes 25, or with one or more auxiliary tubes 25 in various spatial conformations in relation to the mouth 37, and that the auxiliary tubes 25 could vary as to length and diameter, depending upon the specific dental procedure for which use the collector 2 is intended. It is also foreseen that auxiliary tube 25 could be constructed such that it could be removably connected with the apertures 21, in a peg-and-socket type engaging relationship.

The auxiliary tubes 25 are preferably formed of polysilicone, or any other medically acceptable pliable, moisture resistant and substantially fluid impervious material.

During operation of the apparatus 1, the collector 2 is adhesively secured to the face 11 of the patient 7 in a fluid tight engagement therewith. Preferably, the collector 2 has a rectangular cross-section and the engagement surface 15 is generally planar and parallel with the longitudinal axis of the collector 2 and generally perpendicular to the inwardly facing surface 23 associated with the apertures 21. A central axis of each of the apertures 21 generally lies on a line perpendicular to the longitudinal axis of the collector 2.

The collector 2 generally includes adhesion means, that in the present embodiment is illustrated as a double sided adhesive tape 41. An inner adhesion surface 43 of adhesive tape 41 is secured to the engagement surface 15 and is coated with adhesive material acceptable for medical applications. An outer adhesion surface 45 of the adhesive tape 41 is likewise coated with adhesive material acceptable for medical applications and is provided with an easily removed covering 47 for protection of the outer adhesion surface 45 during storage. Just prior to use, the covering 47 is removed to expose the adhesive surface 45 that will be applied to and adhere the face 11, see FIG. 2.

The collector 2 also is operably held in place relative to the face 11 as by the segmented hose 3. In particular, the collector 2 has an outer surface 49 surrounding an outer perimeter thereof having attached thereto at opposite lateral sides thereof first ends 51 of a pair of flexible tubular members 53 of the hose 3 which extend laterally around the perimeter of a patient's head 55 and a slidable clasp 57 for drawing the tubular members 53 together at the back of the head 55, thereby serving as adjustable tensioning means for positioning said collector 2 in a generally surrounding relation to the perioral area 17 of the face 11 while biasing said collector 2 against the face 11 of the patient 7. The collector 2 and tubular members 53 joined together by the clasp 57 form a size adjustment opening 59, which may be increased or decreased in size to conform with the dimensions of the head 55 of the patient 7 and for variance during application and removal.

The tubular members 53 have therein a central axially extending lumen or chamber 61 operably flow connected with the internal channel 19 of the collector 2. The tubular members 53 are constructed of any suitable tubular material which is moisture resistant and substantially fluid impervious. The clasp 57 may be of the kind commonly available for positioning surgical hose. Insertable into the chambers 61 at second ends 63 of the tubular members 53 are the arms or first ends 65 of a "Y" shaped connector 67 for flow connecting the tubular members 53 to a first end 69 of a first connecting hose 71 in such a manner as to allow flow of gases, aerosols and fluids through the apertures 21 and openings 33 of auxiliary tubes 25 and into the internal channel 19 of the collector 2, to flow into the chambers 61 associated with the tubular members 53 and therefrom through the connector 61 and into an interior lumen 73 associated with the first connecting hose 71.

The connector 67 has a pair of arms or first ends 65 frictionally received in the second ends 63 of the tubular members 53, and has a base or second end 75 around which the first connecting hose 71 is secured such that the internal lumen 73 thereof is in flow communication with the chamber 61. The collector 67 is preferably a molded plastic fitting of the type commonly available for connecting surgical hose or tubing.

A second end 77 of the first connecting hose 71 is removably connected to an inlet 79 of the filter means 4. The filter means 4 is preferably a small disposable filter adapted to collect and filter gases, aerosols and liquids drawn through the apparatus 1 by the vacuum pump 5. The filter means 4 has an internal filter element and is constructed of any suitable high efficiency filtering material which removes microorganisms and other particulate matter from air passing therethrough. It is foreseen that the filter means 4 may include air filtering means for removing air borne contaminants and charcoal filter means for trailing nitrous oxide and other hazardous gases.

Removably connected to an outlet 81 of the filter means 4 is a first end 83 of a second connecting hose 85. The second connecting hose 85 having therein an axially extending lumen or cavity 87 operably flow connected with the outlet 81 of the filter means 4. The second connecting hose 85 having a second end 89 removably connected to the intake port 91 of the vacuum pump 5. The first connecting hose 71 and second connecting hose 85 are constructed of any suitable tubular material which is moisture resistant and substantially fluid impervious.

The vacuum pump 5 is of any suitable type capable of creating and maintaining a preselected negative pressure at its intake port 91 and discharging into a discharge header 93. Preferably, the vacuum pump 5 has a fluid collecting reservoir 95 for collecting fluids drawn into the vacuum pump 5 during operation thereof.

In use, the collector 2 is positioned and attached to the perioral area 17 of the face 11 of the patient 7. An electric motor 97 of the vacuum pump 5 is activated by activation switch 99 and operated to induce a negative pressure within the conduit means 3 and the annular collector 2 positioned in a surrounding relation to the operation field. While the dental practitioner is conducting dental procedures, fluids and gases emanating from the operating site are drawn into the spaced apertures 21 and the openings 33 in the auxiliary tubes 25, and pass through the inner channel 19 of the collector 2 into chambers 61 of the tubular members 53, and therefrom pass through the first connecting hose 71 and into the filter means 4 whereat substantially all of the gaseous and aerosolized contaminants are removed. Any remaining effluent, including air, is drawn through the second connecting hose 85, into the vacuum pump 5 through the intake port 91 thereof. The fluid component of the effluent drawn away from the operating site passes into a fluid collecting reservoir 94 of the vacuum pump 5, where preferably it is disinfected by chemical means such as hypochlorite solution 95, such as sold under the trademark "Clorox." The filtered and disinfected remaining air exits the vacuum pump 5 through discharge header 93.

It is to be understood that while certain forms of the present invention have been illustrated and described herein, it is not to be limited to the specific forms or arrangement of parts described and shown.

What is claimed and desired to be secured by Letters Patent is as follows:

1. Am apparatus for reducing the potential for contamination of dental practitioners during dental procedures; said apparatus comprising:
    (a) a vacuum drawing conduit sized and shaped to be adapted to be positioned substantially around the outer perimeter of the mouth of a patient and including at least one aperture therein; said aperture being located such that when said conduit is placed about the mouth, said aperture is positioned generally outside of and in close proximity to the mouth;
    (b) said vacuum drawing conduit includes a continuous hollow tubular collector with said aperture therein; said collector being adapted to extend around the perimeter of the patient's mouth during use; said collector having an access opening defined by an inward side of said collector to allow access to a patient's mouth during use; and
    (c) vacuum generating means operably connected to said vacuum drawing conduit for drawing fluids and aerosols emanating from the mouth through said aperture.

2. An apparatus for reducing the potential for contamination of dental practitioners during dental procedures; said apparatus comprising:
    (a) a vacuum drawing conduit sized and shaped to be adapted to be positioned substantially around the outer perimeter of the mouth of a patient;
    (b) vacuum generating means operably connected to said vacuum drawing conduit for drawing fluids and aerosols emanating from the mouth through said aperture;
    (c) said vacuum drawing conduit includes a continuous hollow tubular collector adapted to extend around the perimeter of the patient's mouth and having an access opening through said collector to allow access to the patient's mouth during use, said access being defined by an inward side of said tubular connector;
    (d) a plurality of spaced apertures located along the inward side of said collector and communicating between said access opening and an internal channel in said collector; each of said apertures being positioned generally outside of and in close proximity to the mouth during use of the apparatus; and
    (e) tube means for communicating with said channel such that fluids and aerosols are adapted to be drawn through said apertures to said vacuum generating means.

3. The apparatus according to claim 2, wherein:
    (a) said collector includes at least one flexible and resilient tube projecting from the collector and having a central bore; said tube having a first end and a second end; both of said first and second ends having openings therein connecting with a central lumen of said tube; said opening of said first end adapted to be operably positioned internally in a mouth of a patient for drawing fluids from the mouth of such a patient; said opening of said second end operably flow connected to said internal channel of said collector such that said vacuum generating means operably draws fluids from the mouth of the patient through said resilient tube.

4. The apparatus according to claim 2, wherein:
    (a) said vacuum drawing conduit includes air and fluid exhaust means; said exhaust means having a generally continuous internal channel flow connecting with said apertures of said collector; and
    (b) said vacuum generating means is operably flow connected to said channel for drawing fluids and aerosols therethrough.

5. The apparatus according to claim 4, wherein:
    (a) said exhaust means includes two tubular members having an internal axially extending chamber flow connecting with said apertures of said collector; said tubular members adapted to be positioned to extend around the perimeter of a patient's head thereby defining a size adjustable opening therebetween; said tubular members adjustably joined together behind said patient's head by adjustment means for slidably altering the dimensions of said size adjustable opening.

6. The apparatus according to claim 2, wherein:

(a) said vacuum drawing conduit includes adhesion means for seatably mounting an engagement portion of said collector on a perioral area of a patient's face.

7. The apparatus according to claim 6, wherein:
(a) said adhesion means includes double-sided adhesive tape applied to said engagement portion; said adhesive tape having an inner adhesion surface for adhering to said engagement portion and an outer adhesive surface for securing to the patient in close proximity to said perioral area; said outer adhesion surface covered with a removable nonstick covering during storage.

8. An apparatus as set forth in claim 6, wherein:
(a) said adhesion means includes two tubular members operably connected with said collector and adapted to be positioned to extend around the perimeter of a patient's head thereby defining a size adjustable opening; said tubular members adjustably joined together behind said patient's head by adjustment means for slidably altering the dimension of said size adjustable opening.

9. An apparatus as set forth in claim 6, wherein said adhesion means includes:
(a) a double-sided adhesive tape applied to said engagement portion; said adhesive tape having an inner adhesion surface for adhering to said engagement portion and an outer adhesive surface for securing to the patient in close proximity to said perioral area; said outer adhesion surface covered with a removable non-stick covering during storage; and
(b) a pair of tubular members operably connected with said collector and adapted to extend around the perimeter of a patient's head thereby defining a size adjustable opening; said tubular members adjustably joined together behind said patient's head by adjustment means for slidably altering the dimension of said size adjustable opening.

10. The apparatus according to claim 2, wherein:
(a) said vacuum drawing conduit includes filter means to remove solids and liquids drawn with fluids and aerosols passing through said vacuum drawing conduit during use.

11. The apparatus according to claim 10, wherein:
(a) said filter means includes air filter means for removing air-borne contaminants; and
(b) charcoal filter means for trapping nitrous oxide and charcoal absorbing hazardous gases.

12. The apparatus according to claim 10, wherein:
(a) said filter means includes connection means to allow said filter means to be removably connected to said vacuum drawing conduit.

13. The apparatus according to claim 2, wherein:
(a) said vacuum drawing conduit includes connection means to allow said vacuum drawing conduit to be removably connected to said vacuum generating means.

14. The apparatus according to claim 5, wherein:
(a) said collector has first ends of a pair of tubular members connected thereto; said tubular members having axially extending internal chambers operably flow connected with said internal channel of said collector;
(b) coupler means to connect second ends of each of said tubular members with a first end of a first connecting hose;
(c) a second end of said first connecting hose removably connected to a first end of filter means;
(d) a second end of said filter means removably connected to a first end of a second connecting hose; and
(e) said second connecting hose having a second end removably connected to said vacuum generating means.

15. The apparatus according to claim 14, wherein:
(a) said coupler means comprising a Y shaped member; said Y-shaped member having a first port and a second port adapted to be flow connected at the second ends of said tubular members with respective chambers of said tubular members; said Y-shaped member having a third port adapted to be joined to a first end of a first connecting hose and flow connected with an internal chamber of said first connecting hose through said third port.

16. The apparatus according to claim 2, wherein:
(a) said vacuum generating means comprising an electrically powered vacuum producing apparatus of the type suitable for removing liquids, gases and solids from the environment and having a fluid collecting reservoir therein.

17. The apparatus according to claim 16, wherein:
(a) said fluid collecting reservoir includes chemical means for denaturing viruses.

18. The apparatus according to claim 2, wherein:
(a) said collector includes connection means to allow said collector to be removably connected to said vacuum drawing conduit.

19. An apparatus for preventing the transfer of harmful substances between a patient and a dental practitioner during dental procedures and the like, said apparatus comprising:
(a) a hollow tubular member of continuous configuration having a central access opening adapted to allow access to a mouth of the patient, said access opening defined by an inward side of said tubular member, said tubular member being adapted to be placed in a surrounding relationship to the mouth of the patient;
(b) a plurality of spaced apertures located along said tubular member and facing said access opening; said tubular member having a generally continuous internal channel flow connecting with said apertures; and
(c) vacuum drawing means operably flow connected to said channel for drawing fluid and aerosols from said access opening through said apertures and said channel.

20. An apparatus for reducing the potential for contamination between dental patients and dental practitioners during dental procedures likely to produce both contaminated sprays and aerosols; said apparatus comprising:
(a) a vacuum drawing conduit having;
(1) a continuous hollow tubular collector adapted to be positioned around and in close proximity to the mouth of the patient; said collector having a central opening therethrough adapted to provide access to the mouth of the patient, said central opening defined by an inner boundary of said tubular collector;
(2) a plurality of spaced apertures located along the inner boundary of said collector and communicating between said access opening and an internal channel of said collector;

(3) said collector having at least one flexible and resilient tube extending therefrom and having a central bore; said tube having an opening flow connected to said bore adapted to be near a distal end thereof and being operably positioned for drawing fluids from the mouth of the patient; said tube bore being flow connected to said internal channel of said collector;

(4) a pair of tubular members having first and second ends; said collector having said tubular member first ends connected thereto; said tubular members each having axially extending lumens operably flow connected with said internal channel of said collector;

(5) coupler means to connect said second ends of said tubular members with a first end of a first connecting hose; said coupler means comprising a Y-shaped member; said Y-shaped member connected to a first end of a first connecting hose;

(6) a second end of said first connecting hose removably connected to a first end of filter means; said filter means having an air filter member for removing air borne contaminants and a charcoal filter member for trapping nitrous oxide and charcoal absorbing hazardous gases; and (7) a second end of said filter means removably connected to a first end of a second connecting hose;

(b) vacuum generating means comprising an electrically powered vacuum cleaning apparatus for drawing liquids, gases and solids and having a fluid collecting reservoir therein; a second end of said second connecting hose being flow connected to the inlet of said vacuum generating means; said fluid collecting reservoir including chemical means for denaturing virus; and (c) adhesion means comprising:

(1) a double sided adhesive tape applied to an engagement portion of said collectors; said adhesive tape having an inner adhesion surface adhered to said engagement portion and an outer adhesive surface adapted for securing to the patient; said outer adhesion surface covered with a removable non-stick covering during storage; and (2) said tubular members adapted to operably extend around the perimeter of the patient's head so as to form a size adjustable opening; said tubular members adjustably joined together behind said patient's head by adjustment means for slidably altering the dimension of said size adjustable opening.

21. A method of preventing the exchange of harmful substances between a dental practitioner and a dental patient, while providing visual and hand access by the practitioner to the mouth of the patient; said method comprising the steps of:

(a) providing a vacuum drawing apparatus including an annular collector having a central access opening, defined by an inward side of said annular collector and an internal channel; said channel flow communicating with said access opening through at least one aperture;

(b) placing said annular collector in surrounding relationship to the mouth of said patient;

(c) generating a vacuum to operably draw fluids and aerosols through said annular collector while said annular collector is in a surrounding relationship to the patient's mouth thereby evacuating harmful substances from the region of said patient's mouth.

22. The method according to claim 21, including:

(a) providing a dental aerosol collector apparatus which is fabricated from medically acceptable materials; and (b) affixing said dental aerosol collector apparatus to a patient in a generally surrounding relationship to a mouth of a dental patient.

23. The method according to claim 22, including:

(a) passing fluids drawn through said collector through a reservoir; and (a) providing a chemical means for denaturing viruses operably drawn through said reservoir.

* * * * *